United States Patent [19]

Kimura et al.

[11] 4,254,060

[45] Mar. 3, 1981

[54] PROCESS FOR PRODUCING AN ALIPHATIC AMINE

[75] Inventors: Hiroshi Kimura; Kazuhito Matsutani; Shunichi Tsutsumi, all of Wakayama, Japan

[73] Assignee: Kao Soap Co., Ltd., Tokyo, Japan

[21] Appl. No.: 122,405

[22] Filed: Feb. 19, 1980

[30] Foreign Application Priority Data

Feb. 21, 1979 [JP] Japan .................. 54-19580

[51] Int. Cl.[3] .................... C07C 85/06; C07C 85/08
[52] U.S. Cl. .................... 564/479; 252/471; 252/474; 252/475; 252/476; 564/480
[58] Field of Search .......... 260/583 R, 583 H, 585 B, 260/585 C; 252/471, 474, 475, 476

[56] References Cited

U.S. PATENT DOCUMENTS 4,210,605  7/1980  Hoshino et al. .................. 260/585 B

*Primary Examiner*—John Doll

*Attorney, Agent, or Firm*—Blanchard, Flynn, Thiel, Boutell & Tanis

[57] ABSTRACT

Aliphatic amines are prepared by reacting an aliphatic alcohol or an aliphatic aldehyde, with ammonia or a primary or secondary amine, in the presence of a homogeneous colloidal catalyst prepared by reducing a mixture of components A and B, a mixture of components A and C, or a mixture of components A, B and C, wherein component A is an inner complex salt of copper or silver, or a carboxylate of copper or silver; component B is an inner complex salt of an element of Group VIII of the Periodic Table of Elements, manganese or zinc, or a carboxylate of said element; and component C is a fatty acid or an alkali metal or alkaline earth metal carboxylate. In the case of a mixture of components A and B, the mixture contains at least one of said inner complex salts and at least one of said carboxylates. In the case of a mixture of components A, B and C, the mixture contains at least one of said inner complex salts.

16 Claims, No Drawings

PROCESS FOR PRODUCING AN ALIPHATIC AMINE

This invention relates to a process for preparing an aliphatic amine by reacting an aliphatic alcohol or an aliphatic aldehyde, with ammonia or a primary or secondary aliphatic amine, using a specific catalyst.

More particularly, this invention relates to a process for preparing an aliphatic amine having the following general formula (IV)

where $R_1$ is a straight chain or branched chain, saturated or unsaturated aliphatic group having 7 to 23 carbon atoms, and $R_2$ and $R_3$ each is a hydrogen atom or a straight chain or branched chain, saturated or unsaturated aliphatic group having 1 to 24 carbon atoms;
by reacting an aliphatic alcohol or an aliphatic aldehyde having the following general formula (I) or (II), respectively,

wherein $R_1$ has the same meaning as defined above; with ammonia or a primary or secondary aliphatic amine having the following general formula (III)

where $R_2$ and $R_3$ each have the same meaning as defined above;
characterized in that the reaction is carried out at a reaction temperature of 100° to 350° C., in the presence of or in the absence of hydrogen, using a colloidal catalyst which is superficially homogeneous and which is prepared by reducing with hydrogen or other reducing agents, a mixture consisting essentially of (1) component A in combination with either (2) (a) component B, (2) (b) component C, or (2) (c) with both of component B and component C, that is, mixtures of A plus B, mixtures of A plus C and mixtures of A plus B plus C. The component A is one member or a mixture of two or more members selected from the group consisting of inner complex salts of copper or silver and carboxylates of copper or silver. The component B is one member or a mixture of two or more members selected from the group consisting of inner complex salts of elements of Group VIII of the Periodic Table, manganese or zinc and carboxylates of those elements. Component C is one member or a mixture of two or more members selected from the group consisting of fatty acids and carboxylates of alkali metals or alkaline earth metals. In the case of a combination of the component A with the component B (mixture of A plus B), the mixture contains at least one of said inner complex salts and at least one of said carboxylates. In the case of a combination of the component A with both of components B and C (mixture of A plus B plus C), the mixture contains at least one of said inner complex salts.

Aliphatic amines are substances of high industrial importance that are useful not only as intermediates for surfactants, such as emulsifiers and dispersants, but also as intermediates for preparing rust-preventatives, fungicides, dye-adjuvants and softening agents for fibers, and so forth.

It is well known to prepare amines by reacting alcohols or aldehydes, with ammonia or primary or secondary amines, thereby to obtain amines that are substituted in the manner corresponding to the starting materials employed.

Catalysts used in this reaction are generally called hydrogenation-dehydrogenation catalysts.

These hydrogenation-dehydrogenation catalysts are solid catalysts and, depending on their form, they are used to perform a suspension-type reaction when they are in powder form and to perform a fixed bed-type reaction when they are in molded form. They are used, as catalyst, in a heterogeneous reaction system.

In regard to the catalysts heretofore used for these reactions, various catalysts are disclosed in the prior patents set forth below. All of the prior art catalysts are solid and are used in a heterogeneous reaction system.

U.S. Pat. No. 2,953,601 discloses Raney nickel or nickel supported on alumina as the catalyst, all of which are solid catalysts, and the reaction is carried out in a heterogeneous system, as to the catalysts. In Example 4 of this patent, for instance, there is a disclosure that the use of Raney nickel in an amount of 2.5% (by weight) provides an alcohol conversion of 82% and a tertiary amine yield of 58% in the reaction between isotridecyl alcohol and ammonia.

U.S. Pat. No. 3,223,734 discloses Raney nickel, copper chromium oxide, palladium-carbon, or nickel-diatomaceous earth as catalysts, all of which are solid catalysts, and the reaction is carried out in a heterogeneous system, as to the catalyst. Example 5 of this patent, for instance, discloses that a tertiary amine is obtained with a yield of 63.2%, using 8.4% of copper chromium oxide catalyst, in the reaction of dodecylamine with dodecyl alcohol, and Example 17 discloses that the use of 5% of Raney nickel provides a tertiary amine with a yield of 69.5%.

German Patent Laid-Open Publication No. 1,493,781 uses supported nickel, supported cobalt, and copper chromium oxide catalysts, all of which are solid, and the reaction is carried out in a heterogeneous system. Example 6 of this specification, for instance, discloses that in the reaction of 2-octanol with dimethylamine, using supported nickel catalyst packed in a reaction tube, the conversion is 95% and the selectivity to 2-octyldimethylamine is 71%.

Japanese Patent Laid-Open Publication No. 19 604/1977 uses copper chromium oxide and cobalt-diatomaceous earth catalysts, all of which are solid. Example 1 of this patent publication, for instance, discloses that when 4% of copper chromium oxide catalyst is used in the reaction between 1-dodecanol and dimethylamine, dimethyldodecylamine having a purity of 98% is obtained with a yield of 92.5% with respect to the starting alcohol.

The aforementioned four prior patent specifications and laid-open publications, i.e., U.S. Pat. Nos. 2,953,601 and 3,223,734, German Patent Laid-Open Publication No. 1,493,781 and Japanese Patent Laid-Open Publication No. 19 604/1977, use Raney nickel, supported nickel, supported cobalt, palladium-carbon, copper chromium oxide catalysts and so forth. These catalysts are all solid and the reactions are carried out in heterogeneous systems, as to the catalysts.

Since these solid catalysts have low activities, the amount of the catalyst that must be used is extremely large, ranging from 2.5% to 8.5%. Consequently, these catalysts are not entirely satisfactory from the industrial viewpoint due to various industrial problems involved in the use of them, such as the high cost of production of the catalysts, the necessity for a filtration step, the disposal of the spent catalysts with possible environmental pollution and so forth. They are not always satisfactory, either, in regard to their selectivity, which is one of the most significant reaction factors, together with the catalyst activity.

In order to solve these problems, the inventor of the present invention made intensive studies in search for a catalyst to be used for the abovementioned reaction. As a result, the inventor previously found a highly active and highly selective catalyst which is superficially homogeneous and colloidal, as disclosed in Japanese Patent Application No. 30149/1978, corresponding to U.S. patent application Ser. No. 11 751, filed Feb. 12, 1979.

As a result of further intensive studies, the inventor has now found a novel catalyst which exhibits the same effect as the catalyst disclosed in the abovementioned patent application. The present invention pertains to an improvement of the abovementioned invention.

Namely, the present invention relates to process for producing an aliphatic amine of the formula (IV), substituted correspondingly to the starting reactants (I), (II) and (III), by the reaction between an aliphatic alcohol or an aliphatic aldehyde having the aforementioned general formula (I) or (II), and ammonia or a primary or secondary aliphatic amine having the general formula (III), using, as catalyst, component A in combination with component B, or with component C or with both of components B and C. The component A is at least one member selected from the group consisting of inner complex salts of copper or silver and carboxylates or copper or silver. The component B is at least one member selected from the group consisting of inner complex salts of elements of the Group VIII of the Periodic Table, manganese or zinc and carboxylates of those elements. The component C is at least one member selected from the group consisting of fatty acids and carboxylates of alkali metals or alkaline earth metals. In the case of a catalyst consisting essentially of a mixture of component A and component B, only one of them is an inner complex salt and the other is a carboxylate. In the case of a catalyst consisting essentially of a mixture of components A, B and C, at least one of component A and component B is an inner complex salt.

Before these catalysts are used for the intended amine-forming reaction, they are reduced with hydrogen or other reducing agent in the reaction medium (such as in an aliphatic alcohol, for example) or in other solvents.

The catalyst obtained in this manner is a colloidal catalyst which is apparently homogeneous and hence, possesses entirely different properties from the well-known solid catalysts described above.

For instance, a colloidal catalyst in accordance with the present invention is characterized by its extremely high activity. Amazingly, the activity of the catalyst of the present invention per unit metal weight is several tens of times higher than that of the solid catalysts, such as Raney nickel or copper-chromite. Even when the amount of the invention catalyst employed is as low as several hundred parts per million (ppm) relative to the starting alcohol or aldehyde, it is sufficient to cause the reaction to proceed. The catalyst in accordance with the present invention makes it possible for the reaction to proceed within a short period of time, with a high yield and selectivity, even when the amount of the catalyst metal used is extremely small. Moreover, the used or spent catalyst can be regenerated for reuse. For this reason, discarding of the catalyst as a spent heavy metal catalyst can be avoided, thereby reducing possible environmental pollution.

The component A used in the present invention is an inner complex salt of copper or silver or a carboxylate of copper or silver. As ligand materials capable of forming an inner complex salt to be used in the inner complex salt of the present invention, mentioned can be made of $\beta$-diketones, glyoximes, glycine, salicylaldehyde, $\alpha$-picolinic acid, $\alpha$-benzoin oxime and the like. However, those ligand materials which contain a hydrogenation poison, such as halogen or sulfur, cannot be used. For example, metal complexes of dimethyldithiocarbamic acid cannot be used because sulfur functions as a catalyst poison.

The preferred ligand materials are $\beta$-diketones and glyoximes and preferred examples of the inner complex salt are copper-acetylacetone complex, silver-acetylacetone complex, and so forth.

As the carboxylic acid for forming the carboxylates, within the scope of component A, any carboxylic acids can be used so long as they contain a carboxyl group or groups in their molecule. In other words, the carboxylic acids can be an aromatic carboxylic acid, or they can have a branched or straight chain alkyl group, a plurality of carboxylic groups or other substituents. Among them, carboxylic acids having 5 to 36 carbon atoms are preferred. They can be natural or synthetic materials and, as examples, there can be mentioned valeric acid, caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, arachic acid, behenic acid, oleic acid and similar compounds having two or more carboxylic groups in the molecule.

The component B used in the present invention is an inner complex salt or a carboxylate of a metal selected from the group consisting of elements of Group VIII of the Periodic Table of Elements, such as nickel, cobalt, iron, palladium and the like, and manganese and zinc. As examples of ligands and carboxylic acids for forming the inner complex salt and carboxylates of those elements, mention can be made of the aforementioned ligands and carboxylic acids. Preferred examples of the inner complex salt and carboxylate are nickel-acetylacetone complex and nickel stearate, respectively.

The component C used in the present invention is a fatty acid or an alkali metal or alkaline earth metal carboxylate of a fatty acid. Examples of the fatty acid include carboxylic acids having 5 to 36 carbon atoms, such as capric acid, lauric acid and stearic acid. Examples of the carboxylates include carboxylates of alkali or alkaline earth metals such as sodium, potassium, magnesium, calcium, barium and the like. Specific examples of such carboxylates are barium stearate and barium laurate.

As the catalyst of the present invention, one consisting of a combination of at least one each of the components A and C can be used. For example, the catalyst can consist essentially of the combination of copper acetylacetone and stearic acid. Preferably, however, the catalyst consists of at least one member selected from component A and component B, wherein either one of A and B is an inner complex salt. The activity of a catalyst of copper stearate soap and nickel acetylacetone is greater than that of a catalyst consisting of the combination of at least one component A and one component C. More preferably, the catalyst consists essentially of the combination of components A, B and C, and wherein at least one of A and B is an inner complex salt. For example, a catalyst consisting of the combination of copper stearate soap, nickel acetylacetone and barium stearate has a higher activity and longer durability than a combined catalyst A plus C or A plus B and, moreover, the colloidal catalyst is further stabilized. Each of components A, B and C may comprise a plurality of compounds.

In the present invention, the mixing proportion of components A, B and C can be optionally determined. It is preferred, however, that the proportion of the component A in the catalyst as a whole is at least 10 mol %, calculated on the basis of the inner complex salt of the metal or the carboxylate. The amount to be used is from 0.001 to 5%, preferably 0.01 to 1%, calculated as the catalyst metal.

Before using the catalyst, the catalyst in accordance with the present invention is dissolved in advance in the reaction medium (such as alcohol) or in a solvent and is reduced with hydrogen or such reducing agents as $Al(C_2H_5)_3$ and $(C_2H_5)_2Al(OC_2H_5)$. Preferably, the catalyst is dissolved in the reaction medium and is reduced with hydrogen at a temperature of 100° to 200° C. Reduction is very easy and is completed within a short period of time while the temperature is raised to 100° to 200° C. The catalyst obtained in this manner is a colloidal catalyst which is apparently homogeneous and which cannot be separated by the ordinary filtration procedures.

After the catalyst is reduced and is converted into the apparently homogeneous and colloidal catalyst, ammonia, dimethylamine or a primary or secondary amine, as the starting reactant materials for preparing the desired substituted amine, are added to the reaction system. The progress of the reaction can be judged from produced water.

The reaction proceeds even in the absence of hydrogen. In the case of the reaction between an alcohol and dimethylamine, for instance, the reaction proceeds simply by adding dimethylamine alone after the reduction of the catalyst in the alcohol. It is preferred, however, that the reaction be carried out in the presence of a small amount of hydrogen because the amounts of by-products having a higher boiling point are reduced and the reaction time is reduced to some extent.

When kept in contact with water for an extended period, the catalyst of the present invention undergoes lowering of the catalytic activity. It is therefore advisable to remove continuously the water formed during the reaction out of the reaction system.

The reaction temperature is from 100° to 350° C., preferably from 190° to 240° C. Although the reaction can be carried out under a reduced pressure, the reaction pressure is preferably from 0 to 10 atmospheres (gauge pressure) and is more preferably atmospheric pressure.

In the reaction between a long chain aliphatic alcohol and dimethylamine, the conversion of the alcohol is 100% when the reaction is carried out with a ternary catalyst consisting of copper stearate, nickel acetylacetone and barium stearate (copper metal 0.1 wt. %, nickel metal 0.02 wt. % and barium metal 0.04 wt. %, with respect to the alcohol) at a reaction temperature of 210° C. and under atmospheric pressure, for a reaction time of 2 hours. In this case, the intended tertiary amine is obtained with a yield of 96%, with the balance being high-boiling materials. Distillation of the reaction product provides a tertiary amine having a purity of not lower than 99 wt. %.

In view of the results of this reaction, it can be seen that the catalyst of the present invention has a catalytic activity which is several tens of times higher compared with the activity of conventional solid catalysts, and the yield as well as purity of the tertiary amine are extremely high. This demonstrates that in accordance with the present invention, any polymerization reaction of the aldehyde is greatly reduced, that the disproportionation reaction of dimethylamine, or formation of monomethylamine and trimethylamine, hardly occurs and that the catalyst of the present invention is an extremely selective catalyst.

If primary and secondary amines, such as monoalkylamine and monoalkylmethylamine, are present in the long chain monoalkyldimethylamine, these amines cannot be separated by distillation because their vapor pressures are substantially the same to one another. Hence, the purity of the tertiary amine derived from the monoalkyldimethylamine is reduced. Although the tertiary amine can be used by itself on an industrial basis, it is mostly used industrially in the form of a quaternary chloride derivative obtained from the reaction of the tertiary amine with benzyl chloride or methyl chloride. In obtaining such derivatives, the primary and secondary amines that may be present as impurities, if any, have reactivities which are remarkably different from that of the tertiary amine so that they exert significant influences on the reaction rate and the quality of the resulting derivative. For this reason, a severe quality requirement is imposed on the monoalkyldimethylamines that are now commercially sold. In accordance with the process of the present invention, it is possible to limit the quantity of the primary and secondary amines formed to below 0.5 wt. %. Accordingly, the catalyst of the present invention can sufficiently comply with the abovementioned severe quality requirement and is found to be superior to the conventional solid catalysts.

The catalyst used in the reaction of the present invention is extremely stable and maintains its apparently homogeneous and colloidal state even after completion of the reaction. It can be separated as residue, during distillation, and filtration of the reaction product is not necessary. Accordingly, unlike the conventional solid catalysts, it becomes possible to omit the filtration step by using the catalyst of the invention.

After the reaction is completed, the conventional distillation procedure is carried out without filtration of the catalyst in order to separate the volatile fraction from the residue. In this residue, the catalyst is present as an apparently homogeneous and colloidal catalyst, which can be used again, as it is, in a subsequent reaction. Even if the reaction is repeated several times in this manner, the catalyst does not exhibit a significant lowering of its catalytic performance.

The reaction of the present invention can be carried out either batchwise or continuously.

In the case of the batchwise reaction, for example, it is not necessary to use a specific stirrer because the catalyst is apparently homogeneous and colloidal. In the case of the continuous reaction, no specific stirrer is required, either, and a gas stirring type can suffice to agitate the reaction mixture.

If a still is fitted to the reactor, in the case of the batchwise reaction, distillation can be performed after the reaction is completed without withdrawing the catalyst. The distillation residue remaining in the still can be used for a subsequent reaction simply by adding fresh reactant materials without performing a reduction procedure on the catalyst. In this manner, the use of the catalyst of the present invention also contributes to a marked simplification of the reaction equipment.

The reactant materials used for the present invention are straight chain or branched chain, saturated or unsaturated aliphatic alcohols such as octyl alcohol, lauryl alcohol, myristyl alcohol, cetyl alcohol, oleyl alcohol, stearyl alcohol and the like, mixtures thereof, Ziegler alcohols obtained by the Ziegler process, oxo alcohols obtained by oxo-synthesis, and so forth. Alternatively, straight chain or branched chain, saturated or unsaturated aliphatic aldehydes such as lauryl aldehyde and oxoaldehyde can be used in place of the alcohols.

The aliphatic amines to be reacted with these alcohols or aldehydes are primary amines such as methylamine, ethylamine, dodecylamine, octadecylamine, etc., and secondary amines such as dimethylamine, diethylamine, didodecylamine, dioctadecylamine and the like. Ammonia can be used in place of the aliphatic amines.

Hereinafter, the present invention will be further explained more definitely by reference to illustrative Examples thereof. As controls, comparative examples are also described which use copper chromite and Raney nickel catalysts.

EXAMPLE 1

Into a 1,000 ml flask equipped with a condenser and a separator for the separation of the reaction water are charged 300 g of dodecanol, 1.25 g of copper acetylacetone (0.10% calculated as copper metal, based on the alcohol charged) and 1 g of stearic acid. The system is purged with nitrogen while the stirrer is rotated, and the temperature is raised. When the temperature reaches 100° C., hydrogen gas is bubbled into the system at a velocity of 60 l/hr through a flow meter. It takes about 40 minutes before the temperature reaches 210° C., during which time copper acetylacetone is reduced and is converted into an apparently homogeneous and colloidal catalyst. While the reaction temperature is kept at 210° C., a mixed gas of dimethylamine and hydrogen (dimethylamine concentration=29 wt. %) is bubbled in at a velocity of 85 l/hr. The reaction water and the oily matter that are distilled out are passed through the condenser and the separator, and the oily matter is continuously fed back to the reactor. The reaction product after five hours' reaction is analyzed by amine value and gas chromatography. The results are set forth below:

| dimethyldodecylamine | 54.5 wt. % |
|---|---|
| unreacted alcohol | 31.5 wt. % |
| high-boiling matters (didodecyl-methylamine, aldol condensates, etc.) | 14.0 wt. % |

The term "%" used hereinafter means "% by weight".

EXAMPLE 2

Using the same equipment as used in Example 1, 300 g of dodecanol, 3 g of copper stearate (0.1% calculated as copper metal, based on the alcohol charged) and 0.6 g of barium stearate are charged into the reactor. The reaction is carried out for five hours under the same reducing conditions and the same operation conditions as in Example 1. The results are as follows:

| dimethyldodecylamine | 71.1% |
|---|---|
| unreacted alcohol | 16.7% |
| high-boiling matters | 12.2% |

From the results of Examples 1 and 2, it can be seen that the catalyst obtained by combining component A with component C can sufficiently ensure the progress of the reaction.

EXAMPLE 3

Using the same equipment as used in Example 1, 300 g of dodecanol, 1.25 g of copper acetylacetone (0.10% calculated as copper metal, based on the alcohol charged) and 1.2 g of nickel stearate (0.04% calculated as nickel metal, based on the alcohol charged) are charged into the reactor and the catalyst is reduced under the same conditions as described in Example 1. As a result, copper acetylacetone and nickel stearate are converted into an apparently homogeneous and colloidal catalyst.

A mixed gas of dimethylamine and hydrogen (concentration of dimethylamine=29%) is bubbled in at the reaction temperature of 210° C., at a velocity of 85 l/hr. The reaction product after five hours' reaction is analyzed with the following results:

| dimethyldodecylamine | 95.9% |
|---|---|
| unreacted alcohol | 1.3% |
| high-boiling matters | 3.8% |

EXAMPLE 4

Using the same equipment as used in Example 1, 300 g of dodecanol, 3.0 g of copper stearate (0.10% calculated as copper metal, based on the alcohol charged) and 0.25 g of nickel acetylacetone (0.02% calculated as nickel metal, based on the alcohol charged) are charged into the reactor and the catalyst is reduced under the same conditions as described in Example 1. As a result, copper stearate and nickel acetylacetone are converted into an apparently homogeneous and colloidal catalyst. The reaction is carried out for 4 hours under the same conditions as in Example 3 with the following results.

| dimethyldodecylamine | 96.1% |
|---|---|
| unreacted alcohol | 0.4% |

-continued

| | |
|---|---|
| high-boiling matters | 3.5% |

From the results of Examples 3 and 4, it can be seen that the mixed catalyst obtained by the combination of component A and component B (with the proviso that only one of them is an inner complex salt is extremely effective for achieving a good reaction, in a short time, with the amounts of metals used being 0.1% Cu and 0.2 to 0.4% Ni.

EXAMPLE 5

Using the same reaction equipment as used in Example 1, this Example examines specifically the component B in the catalyst consisting of the components A, B and C in combination. As the component A, 3.0 g of copper stearate (0.10% calculated as copper metal, based on the alcohol charged) is used, while 0.6 g of barium stearate (0.04% calculated as barium metal, based on the alcohol charged) is used as the component C. As the component B, various nickel or cobalt complexes shown in Table 1 are used in an amount of 0.02%, for each Run, calculated as nickel or cobalt metal, based on the alcohol charged. The reduction conditions for preparing the catalyst are the same as in Example 1. Then, a mixed gas of dimethylamine and hydrogen (dimethylamine concentration=66%) is caused to flow into the reaction mixture, at a velocity of 53 l hr, at a reaction temperature of 210° C. The reaction product after two hours' reaction in each Run is analyzed with the results as set forth in Table 1 below.

TABLE 1

| | | Reaction Product Composition (%) | | |
|---|---|---|---|---|
| Run No. | Component B Nickel or cobalt complex | Dimethyl-dodecyl-amine | Un-reacted alcohol | High boil-ing-point substances |
| 1 | Nickel dimethyl glyoxime | 94.8 | 2.0 | 3.2 |
| 2 | Nickel acetyl-acetone | 96.3 | 0.0 | 3.7 |
| 3 | Nickel dimethyl dithiocarbon-ate (comparison) | 0 | 100 | 0 |
| 4 | Cobalt acetyl-acetone | 58.9 | 38.8 | 2.3 |

As a result, it can be seen that the mixed catalysts obtained by combining components A, B and C are extremely excellent in both catalytic activity and selectivity, except the one of Run No. 3. It can also be seen from the result of Run No. 3 that the component B, in which the ligand forming an inner complex salt contains a catalyst poison such as sulfur, cannot be used as the catalyst of the present invention.

EXAMPLE 6

Using the same equipment as used in Example 1, this Example examines the component C in catalysts consisting of the components A, B and C in combination. As the component A, 2.5 g of copper acetylacetone (0.20% calculated as copper metal, based on the alcohol charged) is used while 0.25 g of nickel acetylacetone (0.02% calculated as nickel metal, based on the alcohol charged) is used as the component B. The amount of stearic acid, as component C, is changed as shown in Table 2. The reduction conditions used of the catalyst are the same as in Example 1. As a result, all the catalysts are converted into apparently homogeneous and colloidal catalysts, except the one of Run No. 5 wherein stearic acid is not added. A mixed gas of hydrogen and dimethylamine (dimethylamine concentration=29%) is bubbled into the reaction system at a velocity of 85 l/hr, at a reaction temperature of 210° C. The reaction product after 3.5 hours' reaction in each Run is examined with the result being set forth in Table 2 below.

TABLE 2

| | Component C | Reaction product composition (%) | | |
|---|---|---|---|---|
| Run No. | Amount of stearic acid added | Dimethyl-dodecyl-amine | Unreacted alcohol | High-boiling matters |
| 5 | 0 g (comparison) | 0 | 100 | 0 |
| 6 | 0.5 g | 70.6 | 27.3 | 2.1 |
| 7 | 1.0 g | 96.1 | 0.3 | 3.6 |
| 8 | 2.0 g | 95.8 | 0.3 | 3.9 |
| 9 | 4.0 g | 96.0 | 0.4 | 4.0 |

As a result, it can be seen that in the combination of components A and B, wherein both are intramolecular complexes such as copper acetylacetone as component A and nickel acetylacetone as component B, there can be obtained a catalyst which can be used effectively for the reaction of the present invention, if component C is added to the combination of components A and B.

COMPARATIVE EXAMPLE 1

The reaction is carried out with Raney nickel as catalyst. Into the reaction equipment of Example 1 are charged 300 g of dodecanol and 12 g of the Raney nickel catalyst (4% calculated as nickel metal, based on the alcohol charged) which is obtained by developing Raney alloy with caustic soda. The reaction is carried out under the same reaction conditions as in Example 1. After two hours' reaction, the reaction product has the following composition:

| | |
|---|---|
| dimethyldodecylamine | 44.1% |
| didodecylamine | 29.8% |
| tridecylamine | 6.7% |
| unreacted alcohol | 11.3% |
| other high-boiling matters | 8.1% |

As a result, it can be seen that although the amount of the Raney catalyst used is much greater, in comparison with the catalyst of the present invention, it has low reactivity and extremely low selectivity.

COMPARATIVE EXAMPLE 2

The reaction is carried out with copper chromite as catalyst. Into the reaction equipment of Example 1 are charged 300 g of dodecanol and 12 g of the copper chromite catalyst (about 1.6% calculated as copper metal, based on the alcohol charged) as a catalyst, and a mixed gas of hydrogen and dimethylamine (dimethylamine concentration=66%) is bubbled into the reaction system at a velocity of 53 l/hr, at a reaction temperature of 210° C. After eight hours' reaction, the reaction product has the following composition:

| | |
|---|---|
| dimethyldodecylamine | 77.2% |
| unreacted alcohol | 2.1% |

| | |
|---|---|
| -continued | |
| other high-boiling matters | 20.7% |

As a result, it can be seen that although the amount of the copper chromite catalyst used is much greater, in comparison with the catalyst of the present invention, it has low reactivity and low selectivity.

The embodiments of the invention in which an exclusive property or privilege is claimed are defined as follows:

1. In a process for preparing an aliphatic amine having the formula (IV)

wherein $R_1$ is a straight chain or branched chain, saturated or unsaturated aliphatic group having 7 to 23 carbon atoms, and $R_2$ and $R_3$ each is hydrogen or a straight chain or branched chain, saturated or unsaturated aliphatic group having 1 to 24 carbon atoms; which comprises reacting an aliphatic alcohol or an aliphatic aldehyde having the formulas (I) or (II), respectively,

wherein $R_1$ is the same as defined above; with ammonia or a primary or secondary aliphatic amine having the following general formula (III)

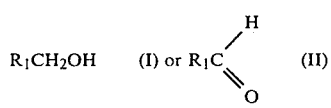

wherein $R_2$ and $R_3$ are the same as defined above; at a temperature of 100° to 350° C., in the presence of a catalyst, the improvement which comprises: said catalyst is a homogeneous colloidal catalyst prepared by reducing with hydrogen or other reducing agent, a mixture of component A and component B wherein said component A is one member or a mixture of two or more members selected from the group consisting of inner complex salts of copper, inner complex salts of silver, carboxylates of copper and carboxylates of silver, and said component B is one member or a mixture of two or more members selected from the group consisting of inner complex salts of an element selected from the group consisting of the elements of Group VIII of the Periodic Table of Elements, manganese and zinc, and carboxylates of said element, with the proviso that among the two kind of components A and B, one component is an inner complex salt and the other is a said carboxylate.

2. In a process for preparing an aliphatic amine having the formula (IV)

wherein $R_1$ is a straight chain or branched chain, saturated or unsaturated aliphatic group having 7 to 23 carbon atoms, and $R_2$ and $R_3$ each is hydrogen or a straight chain or branched chain, saturated or unsaturated aliphatic group having 1 to 24 carbon atoms; which comprises reacting an aliphatic alcohol or an aliphatic aldehyde having the formulas (I) or (II), respectively,

wherein $R_1$ is the same as defined above; with ammonia or a primary or secondary aliphatic amine having the following general formula (III)

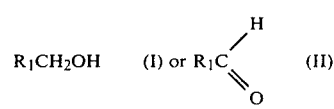

wherein $R_2$ and $R_3$ each are the same as defined above; at a temperature of 100° to 350° C., in the presence of a catalyst, the improvement which comprises: said catalyst is a homogeneous colloidal catalyst prepared by reducing with hydrogen or other reducing agent, a mixture of component A and component C, wherein said component A is one member or a mixture of two or more members selected from the group consisting of inner complex salts of copper, innter complex salts of silver, carboxylates of copper and carboxylates of silver, and said component C is one member or a mixture of two or more members selected from the group consisting of fatty acids, carboxylates of alkali metals and carboxylates of alkaline earth metals.

3. A process according to claim 1 or 2 wherein the ligand material forming said inner complex salt is a $\beta$-diketone.

4. A process according to claim 1 or 2 wherein said fatty acid and the carboxylic acid moiety of said carboxylates are carboxylic acids having 5 to 36 carbon atoms.

5. A process according to claim 4 wherein said carboxylic acid moiety of said carboxylates is an aliphatic carboxylic acid having 5 to 22 carbon atoms.

6. A process according to claim 3 wherein ligand material forming said inner complex salt is acetylacetone.

7. A process according to claim 1 wherein said elements of Group VIII of the Periodic Table of Elements are nickel, cobalt, iron or palladium.

8. In a process for preparing an aliphatic amine having the formula (IV)

wherein $R_1$ is a straight chain or branched chain, saturated or unsaturated aliphatic group having 7 to 23 carbon atoms, and $R_2$ and $R_3$ each is hydrogen or a straight chain or branched chain, saturated or unsaturated aliphatic group having 1 to 24 carbon atoms; which comprises reacting an aliphatic alcohol or an aliphatic aldehyde having the formulas (I) or (II), respectively,

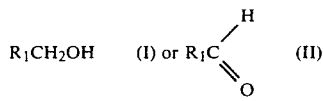

wherein $R_1$ is the same as defined above; with ammonia or a primary or secondary aliphatic amine having the following general formula (III)

wherein $R_2$ and $R_3$ are the same as defined above; at a temperature of 100° to 350° C., in the presence of a catalyst, the improvement which comprises:

said catalyst is a homogeneous colloidal catalyst prepared by reducing with hydrogen or other reducing agent, a mixture of component A, component B and component C, wherein said component A is one member or a mixture of two or more members selected from the group consisting of inner complex salts of copper, inner complex salts of silver, carboxylates of copper and carboxylates of silver, said component B is one member or a mixture of two or more members selected from the group consisting of inner complex salts of an element selected from the group consisting of the elements of Group VIII of the Periodic Table of Elements, manganese and zinc, and carboxylates of said element, and said component C is one member or a mixture of two or more members selected from the group consisting of fatty acids, carboxylates of alkali metals and carboxylates of alkaline earth metals, with the proviso that said mixture contains at least one of said inner complex salts.

9. A process according to claim 8 wherein the ligand material forming said inner complex salt is a β-diketone.

10. A process according to claim 9 wherein the ligand material forming said inner complex salt is acetylacetone.

11. A process according to claim 8 wherein said fatty acid and the carboxylic acid moiety of said carboxylates are carboxylic acids having 5 to 36 carbon atoms.

12. A process according to claim 11 wherein said carboxylic acid moiety of said carboxylates is an aliphatic carboxylic acid having 5 to 22 carbon atoms.

13. A process according to claim 8 wherein said elements of Group VIII of the Periodic Table of Elements are nickel, cobalt, iron or palladium.

14. A process according to claim 1, claim 2 or claim 8 wherein the amount of said catalyst is from 0.001 to 5 wt. %, calculated as the metal, based on the weight of the starting alcohol or aldehyde.

15. A process according to claim 1, claim 2 or claim 8 wherein the amount of said catalyst is from 0.01 to 1.0 wt. %, calculated as the metal, based on the weight of the starting alcohol or aldehyde.

16. A process according to claim 1, claim 2 or claim 8 wherein said catalyst is dissolved in said alcohol or aldehyde in the liquid phase, then hydrogen gas is flowed through the solution of said catalyst in said alcohol or said aldehyde, at a temperature of from about 100° to 200° C. until said catalyst material is reduced and is transformed to a homogeneous colloidal state in said alcohol or aldehyde, and then said ammonia or said primary or secondary aliphatic amine in a gaseous state is bubbled through said alcohol or aldehyde in the liquid phase.

* * * * *